(12) United States Patent
Choi

(10) Patent No.: US 9,289,605 B2
(45) Date of Patent: Mar. 22, 2016

(54) CURRENT APPLICABLE MULTI-NEEDLE SYRINGE, AND AUTOMATIC INJECTION DEVICE

(76) Inventor: Jong-Soo Choi, Seoul (KR)

( * ) Notice: Subject to any disclaimer, the term of this patent is extended or adjusted under 35 U.S.C. 154(b) by 594 days.

(21) Appl. No.: 13/807,217

(22) PCT Filed: Jun. 23, 2011

(86) PCT No.: PCT/KR2011/004602
§ 371 (c)(1),
(2), (4) Date: Dec. 27, 2012

(87) PCT Pub. No.: WO2012/002674
PCT Pub. Date: Jan. 5, 2012

(65) Prior Publication Data
US 2013/0102954 A1 Apr. 25, 2013

(30) Foreign Application Priority Data
Jul. 1, 2010 (KR) .......................... 10-2010-0063254

(51) Int. Cl.
| A61N 1/30 | (2006.01) |
| A61N 1/32 | (2006.01) |
| A61H 39/00 | (2006.01) |
| A61H 39/08 | (2006.01) |

(52) U.S. Cl.
CPC .............. *A61N 1/306* (2013.01); *A61H 39/002* (2013.01); *A61H 39/08* (2013.01); *A61N 1/327* (2013.01); *A61H 2201/105* (2013.01)

(58) Field of Classification Search
CPC ....... A61N 1/306; A61N 1/327; A61N 1/303; A61N 1/00; A61N 1/18; A61N 1/20; A61N 1/30; A61N 1/32; A61H 2201/105; A61H 39/002; A61H 39/08; A61H 2201/00; A61H 2201/10; A61H 2039/005

USPC ........................................................... 604/21
See application file for complete search history.

(56) References Cited

U.S. PATENT DOCUMENTS

| 2010/0030152 A1* | 2/2010 | Lee et al. ........................ 604/131 |
| 2011/0092884 A1* | 4/2011 | Kang ............................... 604/21 |

FOREIGN PATENT DOCUMENTS

| JP | 08308929 A | 11/1996 |
| KR | 100819468 B1 | 4/2008 |
| KR | 100852500 B1 | 8/2008 |
| KR | 100943089 B1 | 2/2010 |

OTHER PUBLICATIONS

International Search Report (PCT/ISA/210) for International Application No. PCT/KR2011/004602 dated Feb. 24, 2012.

* cited by examiner

*Primary Examiner* — Jason Flick
(74) *Attorney, Agent, or Firm* — Harness, Dickey & Pierce, P.L.C.

(57) ABSTRACT

Disclosed is an electrical signal applicable multi-needle syringe. The present invention comprises: a hollow cylinder; a needle hub closely coupled to the rear end of the cylinder; a plurality of needles placed at regular intervals inside the cylinder in such a way that the front ends are further protruded compared with the front end of the cylinder and the drug which is injected through the needle hub is sucked through the rear ends; a first electrode stored inside the cylinder, and commonly connected to a part of the plurality of needles; and a second electrode stored inside the cylinder, and commonly connected with the rest of the plurality of needles. Therefore, it is possible to inject a drug and to simultaneously apply a high frequency directly into the skin through a multi-needle injected into the skin by applying a high frequency between the first electrode and the second electrode, thereby promoting the activation of the injected drug.

1 Claim, 5 Drawing Sheets

CURRENT APPLICABLE MULTI-NEEDLE SYRINGE, AND AUTOMATIC INJECTION DEVICE

TECHNICAL FIELD

Example embodiments of the present invention relate to a multi-needle and an automatic injection device. More particularly, example embodiments of the present invention relate to a multi-needle and an automatic injection device capable of applying a high frequency wave to a portion into which a liquid drug is to be injected.

BACKGROUND ART

Recently, various methods of treating skins have been developed to prevent skin aging. Among them, the most typical one is a massage therapy using a material that is beneficial to a skin and includes skin nutrients.

Such a massage therapy for the skin provides an epidermis layer of the skin with nutrients to keep the skin glowing. However, the effect of the massage therapy may not be continued for a long time, and thus there is a disadvantage that regular treatments are required. Further, since the high priced liquid drug has to be used in large quantities, and thus high cost is required.

Another method that is widely used is a manual method that injects a liquid drug into the skin using a syringe or the like. For example, a medical treatment named a "meso therapy" has been introduced in fields of a cellulite, a skin beauty care, a cosmetic surgery, etc. The meso therapy may use a meso-gun to directly inject a liquid drug where various components are mixed into a portion that requires the treatment through fine needles. However, this method consumes a large amount of the liquid drug, and thus high cost is required. Further, ill-effects may occur according to constitutional characteristics of persons, and the skin may be affected adversely.

Still another method has been used which indirectly transfers a high frequency wave or the like from an epidermis layer of a skin to a dermis layer of the skin. However, since the high frequency wave is indirectly provided to the dermis layer through the epidermis layer, this method does not have a large-effect. Further, this method also requires regular treatments, and thus is inconvenient and costly.

Most of conventional methods of treating skins for anti-aging may massage the skin by supplying the nutrients, may apply the liquid drug to the skin, or may provide an indirect stimulus to the skin to prevent skin aging. However, as described above, these conventional methods may not be continued for a long time, may require the high cost because of the consumption of the large amount of the liquid drug, and may cause the ill-effects in some cases.

DISCLOSURE

Technical Problem

To obviate above-mentioned problems, some example embodiments of the present invention provide a current applying multi-needle that activates a cell or a blood vessel by directly applying a high frequency wave to an injected portion, and then injects a liquid drug, thereby improving the efficacy of the liquid drug by activating skin cell tissues.

Other example embodiments of the present invention provide a current applying multi-needle that is readily applicable to an automatic liquid drug injection device.

Still other example embodiments of the present invention provide a current applying multi-needle capable of maximizing the efficacy of the liquid drug while minimizing the consumption of the high priced liquid drug.

Further still other example embodiments of the present invention provide an automatic injection device using the current applying multi-needle.

Further still other example embodiments of the present invention provide an automatic injection device that is selectively used in the liquid drug injection, in the high frequency wave treatments, or in the combination thereof.

Technical Solution

According to an aspect of the present invention, there is provided a multi-needle including a hollow body, a needle hub tightly coupled to a rear end of the body, a plurality of needles disposed at regular intervals inside the body, front ends of the needles protruding from a front end of the body, rear ends of the needles receiving a liquid drug through the needle hub, a first electrode inside the body, the first electrode commonly coupled to a portion of the plurality of the needles, and a second electrode inside the body, the second electrode commonly coupled to another portion of the plurality of the needles.

Accordingly, a high frequency wave is applied between the first electrode and the second electrode, and thus the activation of the injected liquid drug is expedited by applying the high frequency wave by the multi-needle inserted into the skin before injecting the liquid drug.

In example embodiments of the present invention, it is preferable to further include an insulating member between the first electrode and the second electrode. This is preferable to a bipolar high frequency method.

The multi-needle may further include a supporting member where a plurality of through holes are formed at regular intervals, and the plurality of the needles are inserted into the plurality of through holes, respectively. The supporting member may seal the front end of the body. The body may be integrally formed including a supporting plate at the rear end. A plurality of through holes may be formed at regular intervals at the supporting plate, and the plurality of needles may be inserted into the plurality of through holes, respectively. It is preferable that funnel-shaped grooves are formed at rear ends of the through holes formed at the supporting plate, respectively. In order to provide uniform injection pressures to the respective needles, an inner diameter of each funnel-shaped groove may increase as a distance from the rear end of the needle increases. Further, a liquid drug supplying groove may be formed at a front end of the needle hub to maintain a liquid drug injection pressure according to distance from a center liquid drug outlet to the rear ends of the plurality of needles to be uniform.

According to an aspect of the present invention, there is provided an automatic injection device including an electrical signal applying multi-needle, a syringe coupled to a hub of the electrical signal applying multi-needle, and a meso-gun on which the syringe is mounted, the meso-gun configured to move the mounted syringe forward by a preset depth to insert the electrical signal applying multi-needle into a skin, configured to apply a high frequency signal to the electrical signal applying multi-needle, and configured to move a piston of the syringe forward based on a preset liquid drug injection amount.

Advantageous Effects

A high frequency wave applying multi-needle according to example embodiments of the present invention may activate cell tissues of an injected portion with a high frequency wave by applying the high frequency wave to needles that is inserted into a skin, and thus may improve the efficacy of the liquid drug with a very small amount of the liquid drug by expediting the absorption of the injected liquid drug into the cell tissues. Further, the high frequency wave applying multi-needle may reduce the consumption of the high priced liquid drug, thereby reducing the cost of the treatment and noticeably reducing a pain, an ill-effect, or the like. Further, the high frequency wave applying multi-needle may reduce a recovery time after the treatment.

BEST MODE

The present invention is described more fully hereinafter with reference to the accompanying drawings, in which example embodiments of the present invention are shown. The present invention may, however, be embodied in many different forms and should not be construed as limited to the example embodiments set forth herein. Rather, these embodiments are provided so that this disclosure will be thorough and complete, and will fully convey the scope of the present invention to those skilled in the art.

Figure 1:
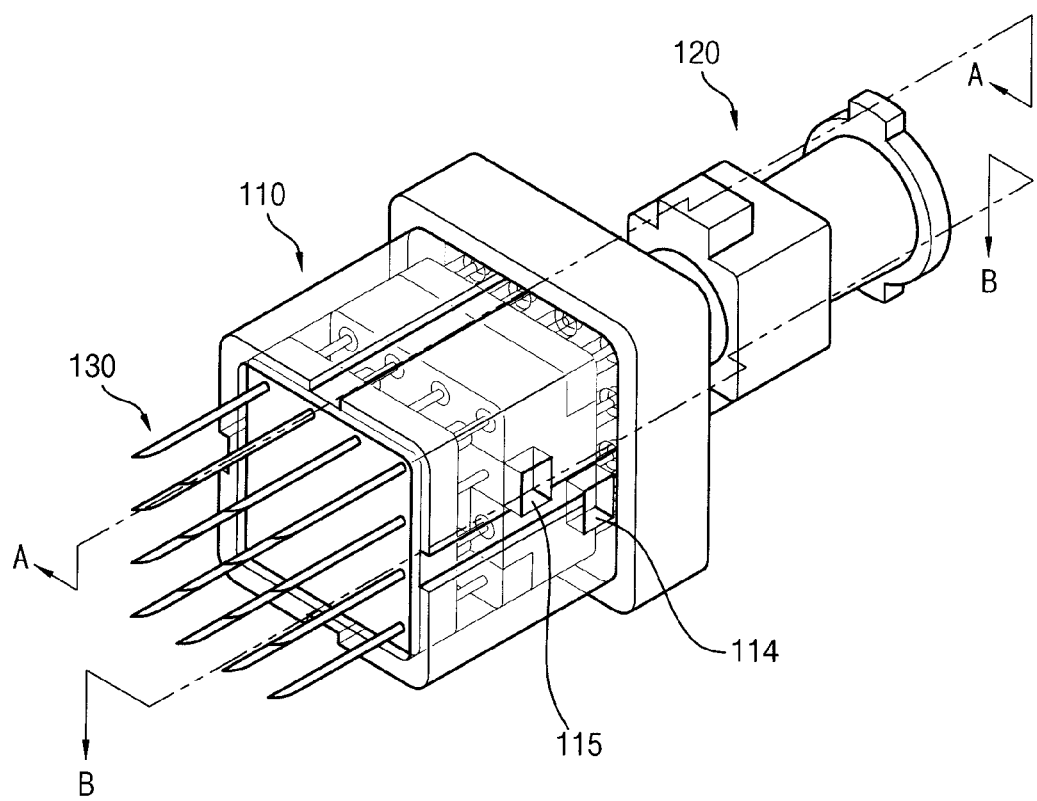
FIG. 1 is a perspective view of a 4*4 multi-needle according to example embodiments of the present invention.
Figure 2:
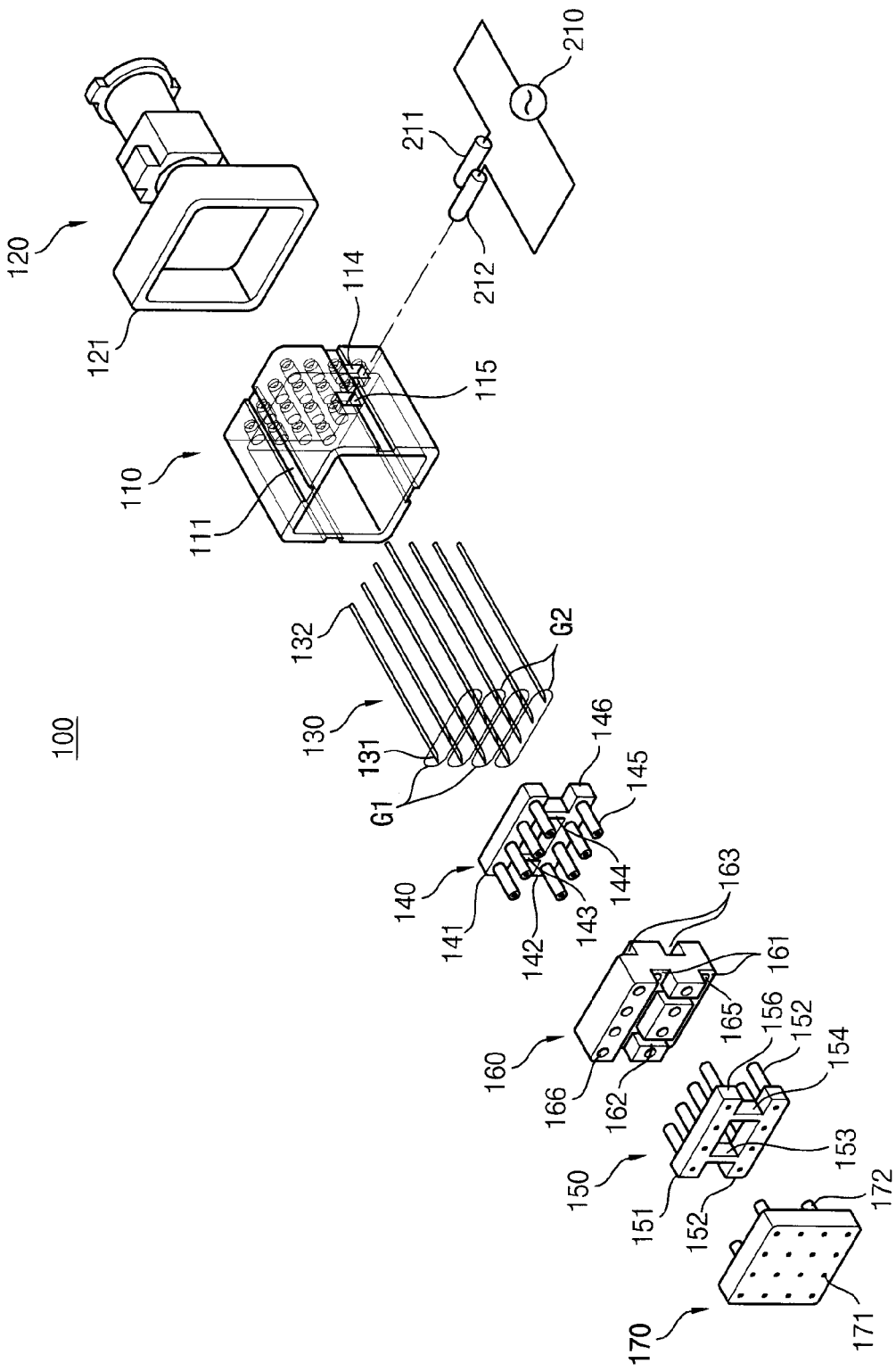
FIG. 2 is an exploded perspective view of a current applying multi-needle of FIG. 1.
Figure 3:
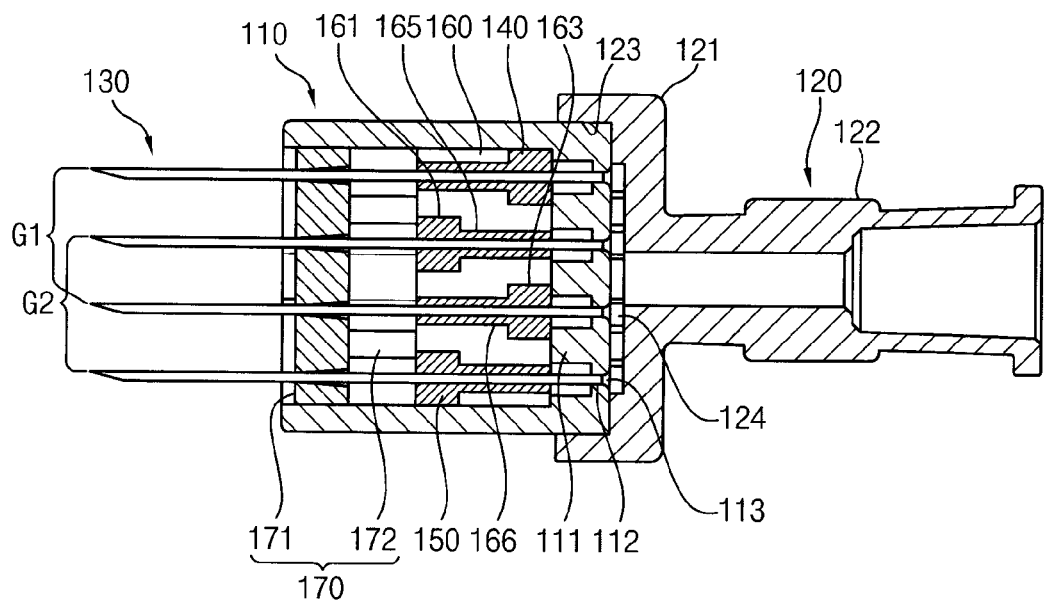
FIG. 3 is a cross-sectional view of a current applying multi-needle of FIG. 1 taken along a line A-A.
Figure 4:
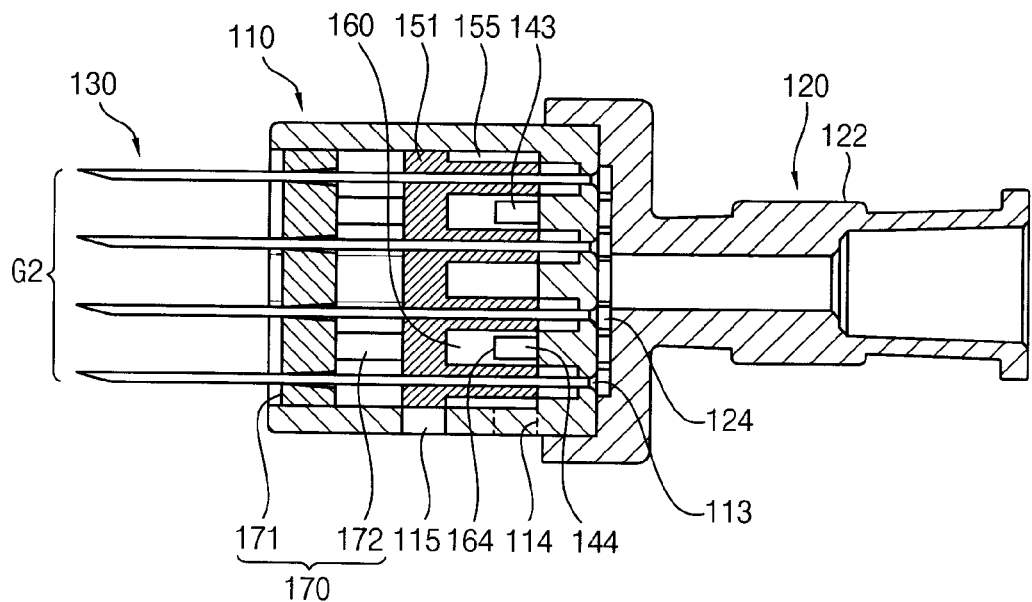
FIG. 4 is a cross-sectional view of a current applying multi-needle of FIG. 1 taken along a line B-B.

FIG. 1 is a perspective view of a high frequency wave applying multi-needle according to example embodiments, FIG. 2 is an exploded perspective view of a high frequency wave applying multi-needle of FIG. 1, FIG. 3 is a cross-sectional view of a high frequency wave applying multi-needle of FIG. 1 taken along a line A-A, and FIG. 4 is a cross-sectional view of a high frequency wave applying multi-needle of FIG. 1 taken along a line B-B.

Referring to FIGS. 1 through 4, a 4*4 high frequency wave applying multi-needle 100 includes a hollow body 110, a needle hub 120 tightly coupled to a rear end of the hollow body 110, sixteen needles 130, a first electrode 140, a second electrode 150, an insulating member 160 and a supporting member 170.

The hollow body 110 may be a square plastic body formed by injection molding. The hollow body 110 may be open at a front end, and may be closed at a rear end by a supporting plate 111 that is integrally formed with side plates. Sixteen supporting holes 112 may be formed at the supporting plate 111, and may be arranged in a 4*4 matrix form. Each supporting hole 112 may have an inner diameter substantially the same as an outer diameter of each needle 130, and thus the supporting hole 112 may support a rear end of the needle 130. A funnel-shaped groove 113 may be formed at a rear end of each supporting hole 112, and an inner diameter of the funnel-shaped groove 113 may increase as a distance from the rear end of the needle 130 increases. The funnel-shaped groove 113 may allow respective needles 130 to have substantially injection pressure regardless of a distance of each needle 130 from the center. Two contact holes 114 and 115 may be formed at one side plate of the hollow body 110. A contact portion 146 of the first electrode 140 may be exposed through one contact hole 114, and a contact portion 156 of the second electrode 150 may be exposed through the other contact hole 115.

The needle hub 120 may include a combination cover 121 and a cylindrical pipe 122 that are integrally formed by plastic injection molding. The cylindrical pipe 122 may extend from the center of the combination cover 121 into the rear. An internal through hole of the cylindrical pipe 122 may penetrate from a back side to a front side of the combination cover 121, and thus may serve as a path for a liquid drug to be injected.

The combination cover 121 may have a square body, and an insertion groove 123 may be formed at the front side of the combination cover 121. The hollow body 110 may be inserted into the insertion groove 123, and thus may be tightly coupled to the combination cover 121. A liquid drug supplying groove 124 may be formed at a surface of the insertion groove 123, and thus the liquid drug provided through the cylindrical pipe 122 may be supplied at substantially the same pressure to rear ends or inlets of the sixteen needles 130. If an initial pressure of the liquid drug varies according to a distance of a needle from the center, or if the initial pressure for a needle located at a peripheral portion is lower than the initial pressure for a needle located at a center portion, a drop of the liquid drug at a tip of the needle located at the center portion may be larger than a drop of the liquid drug at a tip of the needle located at the peripheral portion, which results in a waste of the high priced liquid drug. However, in the present invention, the liquid drug supplying groove 124 may be formed to provide uniform pressure during the initial injection. The liquid drug supplying groove 124 may have various shapes according to the arrangement and the number of the needles 130.

Figure 5:
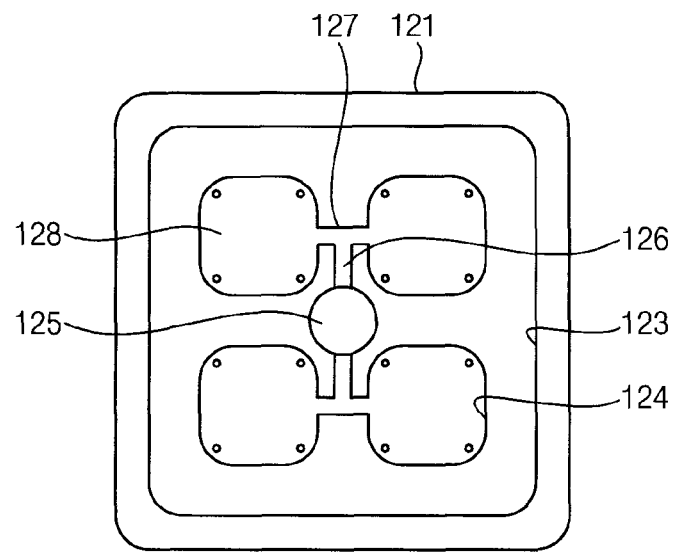
FIG. 5 is a diagram illustrating an example of a liquid drug supplying groove of a 4*4 multi-needle according to example embodiments of the present invention.
Figure 6:
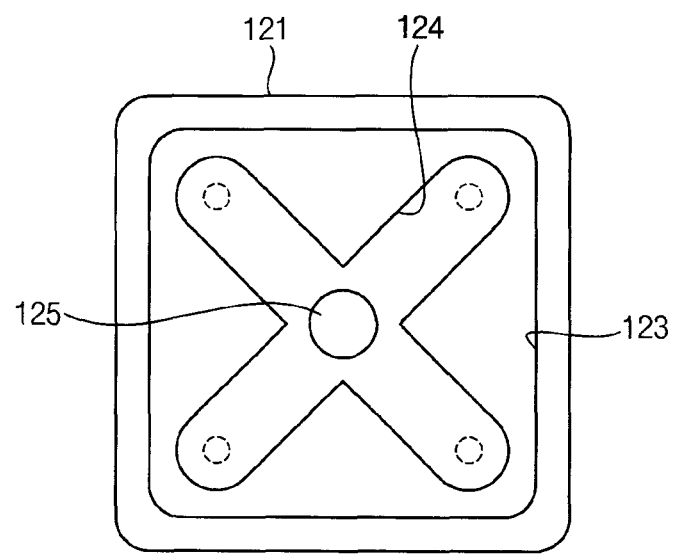
FIG. 6 is a diagram illustrating an example of a liquid drug supplying groove of a 2*2 multi-needle according to example embodiments of the present invention.

FIG. 5 is a diagram illustrating an example of a liquid drug supplying groove of a 4*4 multi-needle according to example embodiments of the present invention, and FIG. 6 is a diagram illustrating an example of a liquid drug supplying groove of a 2*2 multi-needle according to example embodiments of the present invention.

A liquid drug supplying groove 124 of a 4*4 multi-needle may be divided into four partial common grooves 128, and the common grooves 128 may be coupled to a through hole 125 through a horizontal coupling groove 127 and a vertical coupling groove 128. Inlets of four needles may be disposed at four corners of each common groove 128, respectively. Accordingly, the uniform pressure may be provided to the inlets of the respective needles regardless of distances from the through hole 125.

A liquid drug supplying groove 124 of a 2*2 multi-needle may be an X-shaped groove where the through hole 125 is located at the center and inlets of the needles are located at four ends, respectively. Accordingly, since the inlets of the needles are disposed at the same distance from the through hole 125, uniform injection pressure may be provided.

A hitch protrusion may be formed in the middle of the cylindrical pipe 122, and a flange may be formed at the rear end of the cylindrical pipe 122. The hitch protrusion may be coupled to a mounting groove of an automatic injection device. An insertion groove may be formed at the rear end of the cylindrical pipe 122 to receive a front end of a cylinder of a syringe at the same axis with internal through hole of the cylindrical pipe 122.

The sixteen needles 130 may be formed of a conductive material, and may have pipe shapes. Front ends 131 of the needles 130 may be cut at an angle, and rear ends 132 of the needles 130 may be cut perpendicularly. The rear ends 132 of the needles 130 may be stationary fixed to the supporting holes 112.

In the present invention, each needle 130 may include an insulation coated layer formed on an outer surface of a portion inserted into a skin. For example, the insulation coated layer may be formed on a portion contacting an epidermis layer of the skin such that a high frequency current is not provided to the epidermis layer, and the insulation coated layer may not be formed on a portion contacting a reticular layer of a dermis layer of the skin such that the high frequency current is intensively provided to collagen and elastin included in the reticular layer, which is preferable to a bipolar high frequency method.

Such a structure of the needle may allow the collagen and the elastin to be activated by directly stimulating the collagen that is a collagen fiber related to a wrinkle of the skin and the elastin that is an elastic fiber providing the skin with the elasticity using the high frequency current, which results in an improvement of a pharmacological action of an injected drug.

The first electrode 140 may be formed of a conductive material, and may include a pair of horizontal bars 141 and 142, a pair of vertical bars 143 and 144, and eight cylindrical pipes 145. Four cylindrical pipes 145 may be disposed per each horizontal bar 141 and 142, and may protrude from each horizontal bar 141 and 142 in a front direction. A first group G1 of the needles 130 may be inserted and electrically coupled to the cylindrical pipes 145, respectively. The horizontal bars 141 and 142 may be spaced apart from each other by a predetermined gap, and may be supported to have the predetermined gap by the vertical bars 143 and 144. A contact portion 146 of at least one of the horizontal bars 141 and 142 may be exposed through one contact hole 114, and thus may be electrically coupled to one high frequency wave supplying terminal 211.

The second electrode 150 may be formed of a conductive material, and may include a pair of horizontal bars 151 and 152, a pair of vertical bars 153 and 154, and eight cylindrical pipes 155. Four cylindrical pipes 155 may be disposed per each horizontal bar 151 and 152, and may protrude from each horizontal bar 151 and 152 in a front direction. A second group G2 of the needles 130 may be inserted and electrically coupled to the cylindrical pipes 155, respectively. The horizontal bars 151 and 152 may be spaced apart from each other by a predetermined gap, and may be supported to have the predetermined gap by the vertical bars 153 and 154. A contact portion 156 of at least one of the horizontal bars 151 and 152 may be exposed through another contact hole 115, and thus may be electrically coupled to another high frequency wave supplying terminal 212.

Therefore, between the first group G1 including eight needles and the second group G2 including other eight needles, a high frequency wave may be supplied from a power source 210. Further, since the first group G1 and the second group G2 are alternately disposed, the high frequency wave stimulus may be efficiently applied to a corresponding portion.

The insulating member 160 may be disposed between the first electrode 140 and the second electrode 150, and may electrically decouple the first electrode 140 and the second electrode 150, which is preferable to a bipolar high frequency method. At a front side of the insulating member 160, a receiving groove 161 may be formed to receive the horizontal bars 151 and 152 of the second electrode 150, and a receiving groove 162 may be formed to receive the vertical bars 153 and 154 of the second electrode 150. At a back side of the insulating member 160, a receiving groove 163 may be formed to receive the horizontal bars 141 and 142 of the first electrode 140, and a receiving groove 164 may be formed to receive the vertical bars 143 and 144 of the first electrode 140. Eight through holes 165 into which the eight cylindrical pipes 155 are inserted may be formed at a surface of the receiving groove 161, and eight through holes 166 into which the eight cylindrical pipes 145 are inserted may be formed at a surface of the receiving groove 163.

The supporting member 170 may be an insulating plastic square plate formed by injection molding. The supporting member 170 may include sixteen through holes 171 through which the sixteen needles 130 penetrate, and the sixteen through holes 171 may be arranged in a matrix form. At a back side of the supporting member 170, four protrusion bars 172 may be formed to maintain a gap. The supporting member 170 may serve as a final cover that covers a front opening of the hollow body 110, may protect the first electrode 140 and the second electrode 150 inside the body 110, and may support the sixteen needles 160 with a predetermined gap.

An assembly of the needles 130, the first electrode 140, the insulating member 160 and the second electrode 150 may be inserted and fixed using an adhesive inside the body 110, and then may be completely sealed by the supporting member 170 such that moisture or water may not permeate the inside of the body 110. Accordingly, after the multi-needle 100 is assembled, only the contact portions 146 and 156 may be exposed to the outside through one side plate of the body 110.

Figure 7:
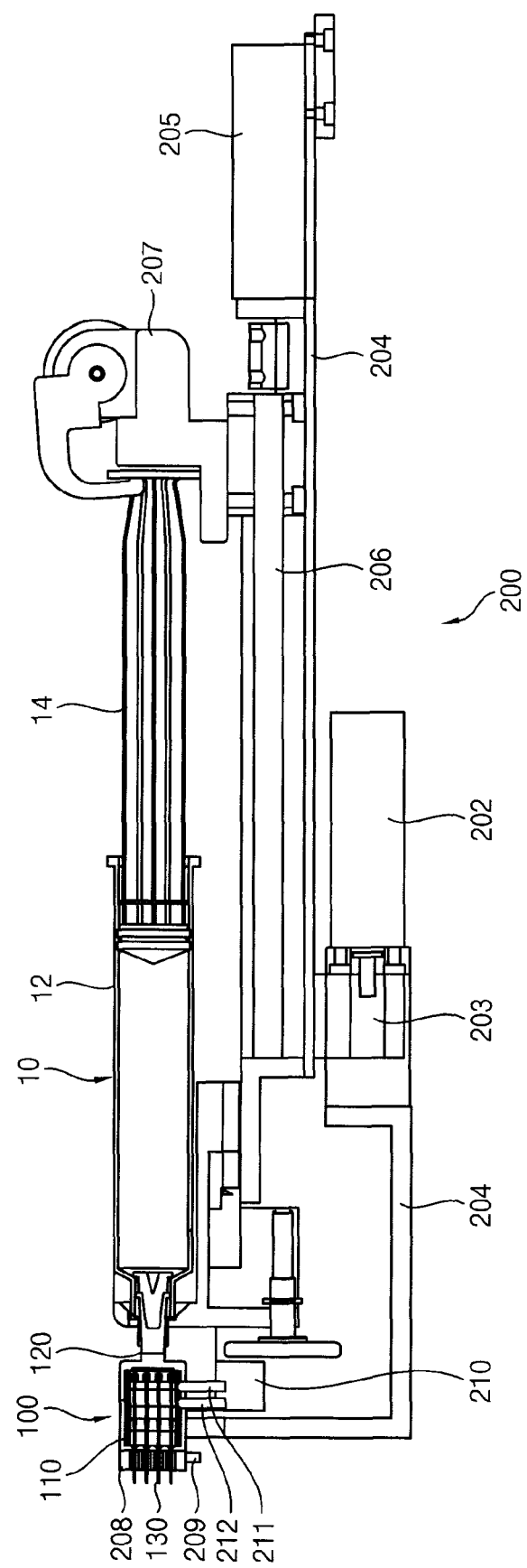
FIG. 7 is a diagram for describing an operation of an automatic injection device according to example embodiments of the present invention.

FIG. 7 is a diagram for describing an operation of an automatic injection device according to example embodiments of the present invention.

An automatic injection device 200 includes a main body 201, a first back and forth moving unit 204 and a second back and forth moving unit 207. A first servomotor 202 and a first gear box 203 may be installed, and the first back and forth moving unit 204 may engage with the first gear box 203 to move back and forth. Further, a second servomotor 205, a high frequency wave generator 210 and a feed rotation shaft 206 may be installed, and the feed rotation shaft 206 may be rotated by the second servomotor 205. The second back and forth moving unit 207 may engage with the feed rotation shaft 206 to move back and forth by normal and inverse rotations of the feed rotation shaft 206.

A suction adapter 208 may be installed at a front end of the main body 201, and a suction tube of an air suction device may be coupled to a tube connecting pipe 209 of the suction adapter 208.

The high frequency wave generator 210 may be installed at a front end of the first back and forth moving unit 204, and the high frequency wave generator 210 may include high frequency wave supplying terminals 211 and 212.

The needle hub 120 of the multi-needle 100 may be coupled to a front end of a cylinder 12 of a syringe 10, and the syringe 10 may be mounted on the first back and forth moving unit 204. The needles 130 may be inserted into the hollow body 110, and the hollow body 110 may be installed in the suction adapter 208. One end of a piston 14 may be fixed to the second back and forth moving unit 207. Ends of the high frequency wave supplying terminals 211 and 212 of the high frequency wave generator 210 may be inserted into the contact holes 114 and 115 of the hollow body 110, and may be coupled to the contact portion 146 of the horizontal bar 142 of the first electrode 140 and the contact portion 156 of the horizontal bar 151 of the second electrode 150 that are exposed in the contact holes 114 and 115, respectively.

After the syringe 10 is mounted as described above, the whole syringe 10 may be moved forward by operating the first servomotor 202 such that front ends of the needles 130 are located at initial injection positions that are substantially the same as a position of a front end of the suction adapter 208.

Subsequently, the cylinder 14 may be moved forward by operating the second servomotor 205 such that a drop of the liquid drug may be formed at the front ends of the needles 130 in an initial injection state to eliminate the air in the needles 130.

After initial setting is completed, a front end of the suction adapter 208 of the automatic injection device 200 may be brought into contact with an injected portion of the skin, and the skin surface may be stuck to the front end of the suction adapter 208 by operating the air suction device to aspirate the air in the suction adapter 208.

Thereafter, the whole syringe 10 may be moved forward by operating the first servomotor 202 so as to insert the needles 130 by a preset depth into the skin. The skin injection depth of the needles 130 may correspond to a length of a portion of each needle 130 that protrudes from the front end of the suction adapter 208.

After the needles 130 are inserted by the injection depth, a high frequency wave may be applied to the needles 130, and thus a high frequency current may flow between the needles G1 coupled to the first electrode 140 and the needles G2 coupled to the second electrode 150. Accordingly, because of the effect of the high frequency massage, tissues and cells of the fine injected portion may be activated without damaging peripheral tissues, and blood vessels of the fine injected portion may be expanded, thereby quickening and improving the efficacy of the liquid drug.

Subsequently, the high frequency current is blocked, and the cylinder 14 may be moved forward by operating the second servomotor 205, so as to inject the liquid drug by a preset injection amount.

As described above, the high frequency wave may be applied to the liquid drug injected portion before injecting the liquid drug such that the cell activation is induced due to the effect of the high frequency massage, and then, if the liquid drug is injected, the permeation of the injected liquid drug may be quicken. Further, the efficacy of the liquid drug may be improved, and the improved efficacy may be obtained by a smaller amount of the liquid drug, thereby reducing the consumption of the high priced liquid drug.

By applying the high frequency wave even after injecting the liquid drug, troubles by the needles or a swelling phenomenon may be rapidly soothed because of the effect of the high frequency massage, which results in the reduction of a recovery time.

Although it is described above that the high frequency wave is applied before the liquid drug is injected according to example embodiments, in other example embodiments, the high frequency wave may be applied before, simultaneously with and/or after injecting the liquid drug.

Further, although the bipolar high frequency method is described above according to example embodiments, in other example embodiments, the multi-needle of the present invention may be used in a monopolar high frequency method. In this case, the same high frequency polarity may be commonly coupled to the first electrode and the second electrode, and the other high frequency polarity may be coupled to a portion of a body other than the injected portion. Accordingly, a broad and deep portion may be affected by the high frequency wave. In case of the monopolar high frequency method, the insulating member 160 may be replaced with a conducting member to electrically connect the first electrode and the second electrode.

Therefore, the multi-needle 100 of the present invention may be applicable to both of the bipolar high frequency method and the monopolar high frequency method. In the bipolar high frequency method, the skin injected portion of each needle except for the tip of the needle may be coated with an insulator. However, since the coating is not required in the monopolar high frequency method, the cost of production of the monopolar high frequency method may be lower than the of the bipolar high frequency method.

The invention claimed is:

1. An automatic injection device comprising:
a multi-needle configured to apply an electrical signal, the multi-needle includes,
a hollow body,
a needle hub tightly coupled to a rear end of the body,
a plurality of needles disposed at regular intervals inside the body, the plurality of needles includes front ends and rear ends, the front ends of the plurality of needles protrude from a front end of the body, the rear ends of the plurality of needles contact a liquid drug through the needle hub,
a first electrode inside the body, the first electrode coupled to a first portion of the plurality of the needles, and
a second electrode inside the body, the second electrode coupled to second portion of the plurality of the needles, the second portion positioned opposite to the first portion;
a syringe coupled to the needle hub of the multi-needle; and
a meso-gun includes high frequency wave supplying terminals respectively coupled to the first electrode and the second electrode, the meso-gun configured to, mount the syringe,
move the syringe forward by a preset depth to insert the multi-needle into a skin,
apply a high frequency current to the multi-needle, and
move forward a piston of the syringe based on a preset liquid drug injection amount,
wherein the high frequency current flows from the first electrode through the first portion of the plurality of the needles, the skin, and the second portion of the plurality of the needles to the second electrode.

* * * * *